United States Patent [19]

Hiyama et al.

[11] Patent Number: 4,864,052
[45] Date of Patent: Sep. 5, 1989

[54] 2,2-DIMETHYLCYCLOPROPANE-CARBOXYLIC ACID DERIVATIVES

[75] Inventors: Tamejiro Hiyama; Makoto Fujita, both of Sagamihara, Japan

[73] Assignee: Sagami Chemical Research Center, Tokyo, Japan

[21] Appl. No.: 183,450

[22] Filed: Apr. 14, 1988

Related U.S. Application Data

[63] Continuation of Ser. No. 907,223, Sep. 15, 1986, abandoned.

[30] Foreign Application Priority Data

Sep. 30, 1985 [JP] Japan .................... 60-214780

[51] Int. Cl.$^4$ .................. C07C 121/66; C07C 69/757
[52] U.S. Cl. ..................... 558/407; 558/29; 558/32; 560/106; 560/107; 560/124
[58] Field of Search ............... 558/407; 560/124

[56] References Cited

U.S. PATENT DOCUMENTS

| | | | |
|---|---|---|---|
| 4,024,163 | 5/1977 | Elliott | 560/124 |
| 4,183,948 | 1/1980 | Huff | 560/124 |
| 4,252,820 | 2/1981 | Lantzsch | 560/124 |
| 4,285,882 | 8/1981 | Kramer | 560/124 |
| 4,307,243 | 12/1981 | Kramer | 560/124 |
| 4,362,744 | 12/1982 | Plummer | 560/124 |
| 4,370,346 | 1/1983 | Punja | 560/124 |
| 4,375,476 | 3/1983 | Cardis | 560/124 |
| 4,385,070 | 5/1983 | Bentley | 560/124 |
| 4,402,973 | 9/1983 | Plummer | 560/124 |

FOREIGN PATENT DOCUMENTS

| | | |
|---|---|---|
| 187674 | 7/1986 | European Pat. Off. . |
| 2351942 | 12/1977 | France . |
| 52-73842 | 6/1977 | Japan .................... 560/124 |
| 2076804 | 12/1981 | United Kingdom . |

OTHER PUBLICATIONS

Itaya, ACS. Symp., Ser., 42, pp. 45-54, (1977).
Arlt, Agnew. Chem. Int. Ed. Engl., 20, pp. 703-722 (1981).

*Primary Examiner*—Michael L. Shippen
*Attorney, Agent, or Firm*—Oblon, Spivak, McClelland, Maier & Neustadt

[57] ABSTRACT

A 2,2-dimethylcyclopropanecarboxylic acid derivative having the formula:

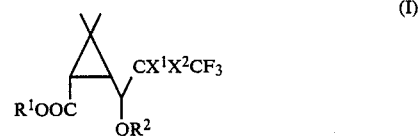

(I)

wherein $R^1$ is an alkyl group or an aryl group, $R^2$ is a hydrogen atom, an acyl group, a sulfonyl group or an alkyl group, and each of $X^1$ and $X^2$ is a halogen atom.

2 Claims, No Drawings

2,2-DIMETHYLCYCLOPROPANE-CARBOXYLIC ACID DERIVATIVES

This application is a continuation of application Ser. No. 907,223, filed on Sept. 15, 1986, now abandoned.

The present invention relates to 2,2-dimethylcyclopropanecarboxylic acid derivatives which are useful as starting materials for 2,2-dimethyl-3-(2-chloro-3,3,3-trifluoro-1-propenyl)cyclopropanecarboxylic acid esters known as fluorine-containing pyrethroid insecticides or intermediates for the synthesis of such insecticides (Japanese Unexamined Patent Publications Nos. 95945/1978, 112820/1979, 130537/1979, 59141/1980, 89248/1980 and 111488/1980).

For the production of 2,2-dimethyl-3-(2-chloro-3,3,3-trifluoro-1-propenyl)cyclopropanecarboxylic acid esters, there have been known (i) a method wherein 1,1,1-trichlorotrifluoroethane is added to ethyl 3,3-dimethyl-4-pentenoate, followed by cyclization and dehydrohalogenation (Japanese Unexamined Patent Publications Nos. 95945/1978, 112820/1979 and 89248/1980), (ii) a method wherein the product is synthesized from 1,1,1-trifluoro-2-chloro-5-methyl-2,4hexadiene or 1,1,1-trifluoro-2,2-dichloro-5-methyl-4hexene and a diazoacetic acid ester (Japanese Unexamined Patent Publications Nos. 95945/1978 and 112820/1979, and J. Mol. Cat., 11, 119 (1981)), and (iii) a method wherein a ring-contraction reaction of 2-chloro-2-(2,2-dichloro-3,3,3-trifluoropropyl)-3,3-dimethylcyclobutanone is utilized (Japanese Unexamined Patent Publication No. 92830/1981). However, each of these methods requires a number of steps, and in the case of method (ii), the synthesis of the starting material is cumbersome. Thus, these methods have a drawback such that they are hardly useful for industrial production.

The present inventors have conducted extensive researches to overcome such drawbacks of the conventional methods and to provide a practical method for the production of 2,2-dimethyl-3-(2-chloro-3,3,3-trifluoro-1-propenyl)cyclopropanecarboxylic acid esters, and have found that 2,2-dimethylcyclopropanecarboxylic acid derivatives, represented by the formula I given hereinafter, are very useful as intermediates for the production of such esters. The present invention has been accomplished on the basis of this discovery.

The present invention provides a 2,2-dimethylcyclopropanecarboxylic acid derivative having the formula:

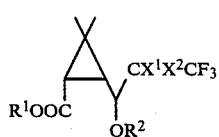

(I)

wherein $R^1$ is an alkyl group or an aryl group, $R^2$ is a hydrogen atom, an acyl group, a sulfonyl group or an alkyl group, and each of $X^1$ and $X^2$ is a halogen atom.

Now, the present invention will be described in detail with reference to the preferred embodiments.

The 2,2-dimethylcyclopropanecarboxylic acid derivative of the formula I of the present invention can be produced, for instance, in accordance with the following reaction scheme.

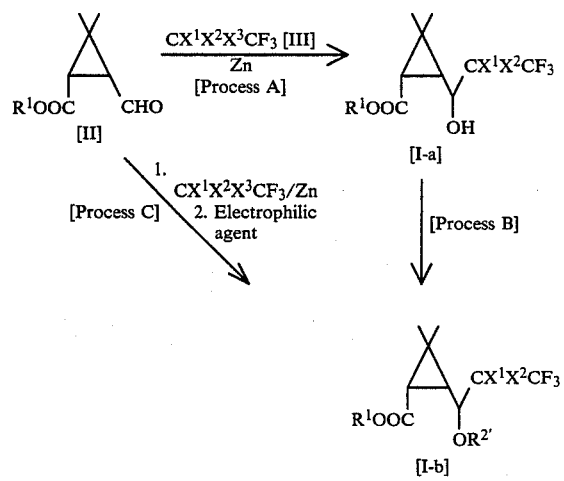

In the above formulas, $R^1$ is an alkyl group or an aryl group, $R^2$, is an acyl group, a sulfonyl group or an alkyl group, and each of $X^1$, $X^2$ and $X^3$ is a halogen atom.

[Process A]

This process comprises reacting a 2,2-dimethyl-3-formylcyclopropanecarboxylic acid ester of the formula II with a 1,1,1-trihalotrifluoroethane of the formula III in the presence of zinc powder, followed by hydrolysis to obtain a 2,2-dimethylcyclopropanecarboxylic acid derivative of the formula I-a. The 2,2-dimethyl-3-formylcyclopropanecarboxylic acid ester of the formula II used as the starting material of this process is a compound which can readily be obtained in good yields, for instance, by the ozonolysis of a chrysanthemic acid ester. For instance, there may be mentioned methyl 2,2-dimethyl-3-formylcyclopropanecarboxylate, ethyl 2,2-dimethyl-3-formylcyclopropanecarboxylate, t-butyl 2,2-dimethyl-3-formylcyclopropanecarboxylate, phenyl 2,2-dimethyl-3-formylcyclopropanecarboxylate, benzyl 2,2-dimethyl-3-formylcyclopropanecarboxylate, 2-methyl-3-phenylbenzyl 2,2-dimethyl-3-formylcyclopropanecarboxylate, 3-phenoxybenzyl 2,2-dimethyl-3-formylcyclopropanecarboxylate, cyano(3-phenoxyphenyl)methyl 2,2-dimethyl-3-formylcyclopropanecarboxylate and pentafluorophenylmethyl 2,2-dimethyl-3-formylcyclopropanecarboxylate. The 1,1,1-trihalotrifluoroethane of the formula III as another starting material, is a compound which is readily commercially available. For instance, it is possible to employ 1,1,1-trichlorotrifluoroethane, 1-bromo-1,1-dichlorotrifluoroethane, 1,1-dibromo-1chlorotrifluoroethane, 1,1,1-tribromotrifluoroethane, 1,1-dichloro-tetrafluoroethane, 1-bromo-1-chlorotetrafluoroethane or 1,1-dibromotetrafluoroethane.

Zinc is preferably used in a powder form usually in an amount of from 0.5 to 2 equivalents, preferably from 1 to 1.5 equivalents.

The reaction is preferably conducted in an aprotic polar solvent. For instance, it is possible to employ an amide such as dimethylformamide or hexamethylphosphoric triamide, or a urea such as N,N-dimethylpropyleneurea, or a sulfoxide such as dimethyl sulfoxide. These solvents may be used in combination with usual aprotic organic solvents.

The reaction proceeds at a temperature of from −20° to 100° C. However, in order to conduct the reaction efficiently, it is preferred to conduct the reaction at a temperature of from 0° to 60° C.

[Process B]

This process comprises reacting a 2,2-dimethylcyclopropanecarboxylic acid derivative of the formula I-a with an acylating agent, a sulfonylating agent or an alkylating agent in the presence of a base to obtain a 2,2-dimethylcyclopropanecarboxylic acid derivative of the formula I-b.

As the acylating, sulfonylating or alkylating agent, there may be employed an acid anhydride such as acetic anhydride, benzoic anhydride, trifluoroacetic anhydride or methanesulfonic anhydride, an acid halide such as acetyl chloride, acetyl bromide, benzoyl chloride, methanesulfonyl chloride or p-toluenesulfonyl chloride, an alkyl halide such as methyl iodide or benzyl bromide, or a sulfuric acid ester such as dimethyl sulfate. The amount used is within a range of from a stoichiometric amount to a large excess, relative to the substrate.

In this process, the reaction is conducted in the presence of a base. As such a base, it is possible to employ a tertiary amine such as pyridine, 2,6-lutidine, triethylamine, diisopropylethylamine or 1,8-diazabicyclo[5,4,0]undec-7-ene, a carbonate such as potassium carbonate or sodium carbonate, or a metal hydride such as sodium hydride or potassium hydride, in a wide range of from the stoichiometric amount to a large excess, relative to the substrate.

The reaction can be conducted in a proper organic solvent or in the absence of a solvent. As the organic solvent, a hydrocarbon solvent such as hexane or benzene, an ether solvent such as diethyl ether or tetrahydrofuran, or an amide solvent such as dimethylformamide, may be employed. They may be used alone or in combination as a mixture.

The reaction proceeds at a temperature of from −50° to 100° C. In order to conduct the reaction efficiently, however, it is preferred to conduct the reaction at a temperature of from 0° to 50° C.

[Process C]

This process comprises reacting a 2,2-dimethyl-3-formylcyclopropanecarboxylic acid ester of the formula II with a 1,1,1-trihalotrifluoroethane of the formula III in the presence of zinc powder, followed by a direct reaction with an electrophilic agent such as acylating agent, a sulfonylating agent or an alkylating agent, to obtain a 2,2-dimethylcyclopropanecarboxylic acid derivative of the formula I-b. As the starting materials of this process i.e. the 2,2-dimethyl-3-formycyclopropanecarboxylic acid ester of the formula II and the 1,1,1-trihalotrifluoroethane of the formula III, those mentioned in process A can be used. Likewise, the reaction conditions such as the amount of the zinc powder, the solvent, the reaction temperature, etc., may be the same as those in process A.

For the electrophilic agent such as the acylating, sulfonylating or alkylating agent, to be used in this process, those mentioned in process B may be employed. These agents may be employed in an amount within a range of from the stoichiometric amount to a large excess relative to the substrate of the formula II. The electrophilic agent may be added within a temperature range of from −50° to 100° C. In order to conduct the reaction efficiently, however, a temperature of from 0° to 50° C. is preferred.

Now, the present invention will be described in further detail in Reference Examples in addition to Examples. However, it should be understood that the present invention is by no means restricted to these specific Examples. REFERENCE EXAMPLE 1

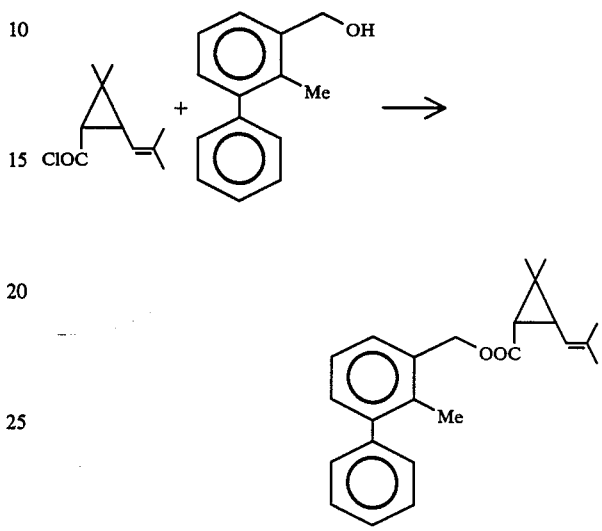

A solution of 2.97 g (15.0 mmol) of (2-methyl-3-phenylphenyl)methanol in 1.5 ml of pyridine and 10 ml of diethyl ether, was dropwise added to a solution of 2.80 g (15.0 mmol) of 2,2-dimethyl-3-(2-methyl-1-propenyl)cyclopropanecarbonyl chloride in 10 ml of diethyl ether, and the mixture was stirred at room temperature for 3 hours. After an addition of 20 ml of hexane thereto, the inorganic salt was filtered off, and the filtrate was concentrated under reduced pressure. The product was purified by column chromatography (silica gel, dichloromethane/hexane=½) to obtain 4.23 g of (2-methyl-3-phenylphenyl)methyl 2,2-dimethyl-3-(2-methyl-1-propenyl)cyclopropanecarboxylate as a colorless oil.

Yield: 81%

$^1$H-NMR (CDCl$_3$) δ 1.14(s, 3H), 1.29(s, 3H), 1.54(d, 1H), 1.71(s, 6H), 2.17(dd, 1H), 2.22(s, 3H), 4.94(d, 1H), 5.20(s, 2H), 7.2–7.6(m, 8H).

IR (neat): 1728, 1193, 1156, 1115, 764, 706 cm$^{-1}$

Elemental analysis: Calculated for $C_{24}H_{28}O_2$: C, 82.72; H, 8.10% Found: C, 82.52; H, 8.14%

REFERENCE EXAMPLES 2 to 4

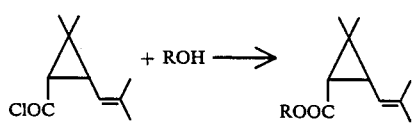

The following esters were obtained in the same manner as in Reference Example 1.

3-Phenoxyphenylmethyl ester

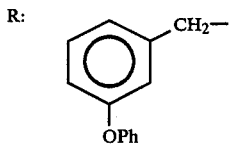

Yield: 98%

¹H-NMR (CDCl₃): (trans-isomer) δ 1.12(s, 3H), 1.24(s, 3H), 1.42 (d, 1H), 1.69(s, 6H), 2.04(dd, 1H), 4.85(d, 1H), 5.04(s, 2H), 6.8–7.4(m, 9H); (cis-isomer) δ 1.18(s, 3H), 1.23(s, 3H), 1.69(s, 6H), 5.03(s, 2H), 5.33(d, 1H), 6.8–7.4(m, 9H)

Cyano(3-phenoxyphenyl)methyl ester

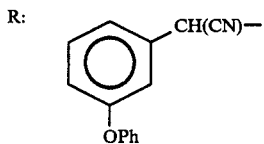

Yield: 64%

¹H-NMR (CDCl₃): (a mixture of trans- and cis-isomers) δ 1.12, 1.16, 1.23, 1.30(s, total 6H), 1.2–1.6(m, 1H), 1.6–1.8(m, 6H), 1.9–2.25(m, 1H), 4.85, 5.27(broad d, total 1H), 6.32, 6.33(s, total 1H), 6.9–7.5(m, 9H)

(Pentafluorophenyl)methyl ester

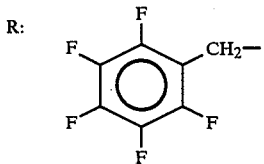

Yield: 85%

¹H-NMR (CDCl₃): (a mixture of trans- and cis-isomers) δ 1.13, 1.19, 1.24, 1.26(s, total 6H), 1.37(d, 1H), 2.05(dd, 1H), 4.85, 5.27(broad d, 1H), 5.10–5.25 (m, 2H)

REFERENCE EXAMPLE 5

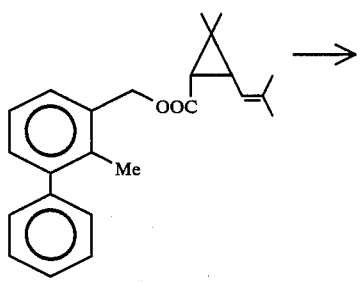

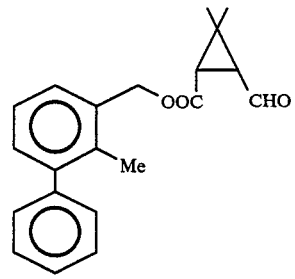

Ozone was bubbled at −78° C. into a solution of 698 mg (2.01 mmol) of (2-methyl-3-phenylphenyl)methyl 2,2-dimethyl-3-(2-methyl-1-propenyl)cyclopropanecarboxylate obtained in Reference Example 1, in 10 ml of ethyl acetate. The supply of ozone was terminated when the solution turned slightly blue. Then, 1 ml of dimethyl sulfide was added, and the temperature of the mixture was allowed to warm to room temperature. The reaction mixture was concentrated under reduced pressure and purified by column chromatography (dichloromethane/hexane=1/1) to obtain 591 mg of (2-methyl-3-phenylphenyl)methyl 2,2-dimethyl-3-formylcyclopropanecarboxylate.

Yield: 92%

¹H-NMR (CDCl₃): (trans-isomer) δ 1.31(s, 3H), 1.36(s, 3H), 2.22(s, 3H), 2.53(d, 1H), 2.53(s, 1H), 5.23(s, 2H), 7.23–7.44(m, 8H), 9.59(dd, 1H) (cis-isomer) δ 1.27(s, 3H), 1.58(s, 3H), 1.88(dd, 1H), 2.20(d, 1H), 2.23(s, 3H), 5.28(s, 2H), 7.23–7.44(m, 8H), 9.79(d, 1H)

IR (neat): 1730, 1709, 1237, 1164, 1113, 763, 704 cm⁻¹

Mass [m/z (%)]: 322(M⁺, trace), 182(18), 181(100), 180(74), 179(16), 178(12), 167(11), 166(56), 165(67), 152(10), 97(61), 43(12), 41(36), 39(13), 27(11)

Elemental analysis: Calculated for $C_{21}H_{22}O_3$ C, 78.23; H, 6.88% Found: C, 77.97; H, 6.92%

REFERENCE EXAMPLE 6

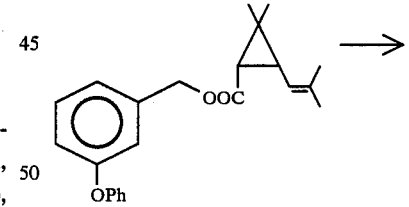

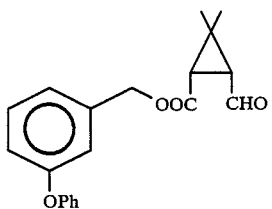

Ozone gas was bubbled at −78° C. into a solution of 3.50 g (10.0 mmol) of 3-phenoxyphenylmethyl 2,2-dimethyl- 3-(2-methyl-1-propenyl)cyclopropanecarboxylate obtained in Reference Example 2, in 20 ml of ethyl acetate. The subsequent operation was conducted in the same manner as those in Reference Example 5, whereby 2.66 g of 3-phenoxyphenylmethyl 2,2-dimethyl-3-formylcyclopropanecarboxylate was obtained as a colorless oil.

Yield: 82%

¹H-NMR (CDCl₃): (trans-isomer): δ 1.29(s, 3H), 1.32(s, 3H), 2.46(ABq, 2H), 5.06(s, 2H), 6.8–7.5(m, 9H), 9.56(dd, 1H) (cis-isomer) δ 1.8–2.3(m, 2H), 9.73(d, 1H) (Other signals were not distinguishable from those of the trans-isomer)

IR (neat): 1732, 1711, 1588, 1492, 1258, 1215, 1167, 693 cm⁻¹

Mass [m/z (%)]: 325(M⁺+1, 5), 324(M⁺, 21), 184(20), 183(100), 97(40), 77(10), 41(10)

Elemental analysis: Calculated for $C_{20}H_{20}O_4$: C, 74.06; H, 6.21% Found: C, 74.08; H, 6.31%

REFERENCE EXAMPLE 7

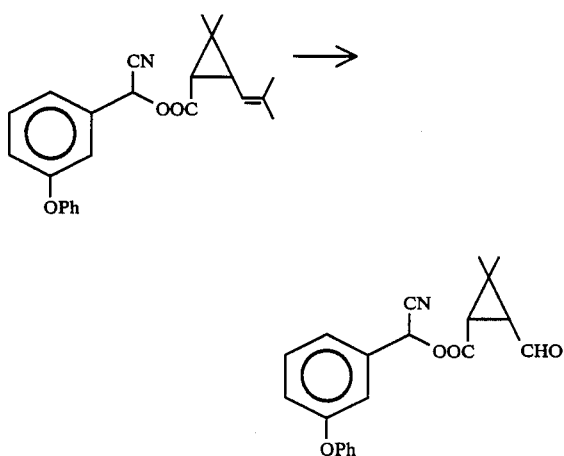

Ozone gas was bubbled at −78° C. into a solution of 1.88 g (5.00 mmol) of cyano(3-phenoxyphenyl)methyl 2,2-dimethyl-3-(2-methyl-1-propenyl)cyclopropanecarboxylate obtained in Reference Example 3, in 10 ml of ethyl acetate. The subsequent operation was conducted in the same manner as in Reference Example 5, whereby 1.26 g of cyano(3-phenoxyphenyl)methyl 2,2-dimethyl-3-formylcyclopropanecarboxylate was obtained as a colorless oil.

Yield: 72%

¹H-NMR (CDCl₃): (a mixture of trans- and cis-isomers) δ 1.27, 1.29, 1.32, 1.38, 1.44, 1.58(s, total 6H), 1.8–2.3, 2.4–2.6(m, total 2H), 6.33, 6.36(s, total 1H), 6.9–7.5(m, 9H), 9.60(dd), 9.70(d, total 1H)

IR (neat): 1748, 1712, 1590, 1492, 1248, 1232, 1148, 698 cm¹

Mass [m/z (%)]: 350 (M⁺+1, 6), 349(M⁺, 21), 209(18), 208(31), 181(62), 180(13), 125(11), 115(10), 113(10), 98(13), 97(100), 95(10), 77(21), 69(14), 67(11), 51(14), (18), 41(32), 39(12), 28(29)

REFERENCE EXAMPLE 8

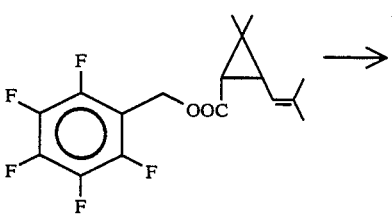

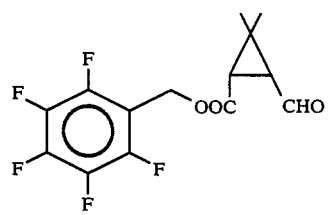

Ozone gas was bubbled at −78° C. into a solution of 3.48 g (10.0 mmol) of pentafluorophenylmethyl 2,2-dimethyl-3-(2-methyl-1-propenyl)cyclopropanecarboxylate obtained in Reference Example 4, in 20 ml of ethyl acetate. The subsequent operation was conducted in the same manner as in Reference Example 5, whereby 2.87 g of pentafluorophenylmethyl 2,2-dimethyl-3-formylcyclopropanecarboxylate was obtained as a colorless oil.

Yield: 89%

¹H-NMR (CDCl₃): (a mixture of trans- and cis-isomers) (trans-isomer) δ 1.30(s, 3H), 1.36(s, 3H), 2.44(d, 1H), 2.49(dd, 1H), 5.15–5.25(m, 2H), 9.58(d, 1H) (cis-isomer) δ 1.55(s, 3H), 1.86(dd, 1H), 2.11(d, 1H), 9.72(d, 1H) (Other signals were not distinguishable from those of the trans-isomer)

¹⁹F-NMR (CDCl₃—CFCl₃): δ −141.8(m, 2F), −152.2(m, 1F), −161.3(m, 2F)

IR (neat): 1740, 1712, 1528, 1512, 1160, 1133, 1056 946 cm⁻¹

Mass [m/z (%)]: 294(M⁺+1, 2), 293(M⁺,11), 181(100), 113(11), 97(90), 69(10), 67(14), 43(17), 41(37), 39(12), 27(11)

EXAMPLE 1

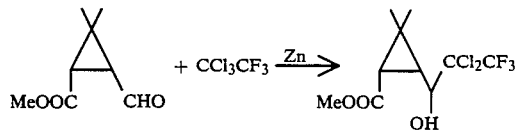

To a solution of 156 mg (1.00 mmol) of methyl 2,2-dimethyl-3-formylcyclopropane carboxylate and 0.226 ml (2.00 mmol) of 1,1,1-trichlorotrifluoroethane in 1 ml of dimethylformamide (DMF), 98 mg (1.50 mmol) of zinc powder was added at 0° C., and the mixture was stirred at 0° C. for 20 minutes, and at 50° C. for 7 hours. Then, 1 ml of a saturated ammonium chloride aqueous solution was added, and the mixture was extracted with diethyl ether (2 ml×5 times). The extract was dried over anhydrous magnesium sulfate, then filtered and concentrated under reduced pressure. The product was purified by thin layer chromatography (silica gel, dichloromethane/hexane=½) to obtain 232 mg of methyl 2,2-dimethyl-3-(1-hydroxy-2,2-dichloro-3,3,3-trifluoropropyl)cyclopropanecarboxylate (a mixture of two stereoisomers in a ratio of 55:45) as a colorless oil.

Yield: 75%

¹H-NMR (CDCl₃): From the spectrum of a mixture of stereoisomers (For the major stereoisomer) δ 1.23(s, 3H), 1.25(s, 3H), 1.71(d, 1H), 1.95(dd, 1H), 2.75(d, 1H), 3.71(s, 3H), 3.83(t, 1H) (For the minor isomer) δ 1.29(s, 3H), 1.33 (s, 3H), 1.72(d, 1H), 1.83(dd, 1H), 2.48(d, 1H), 3.70(s, 3H), 3.83(dd, 1H)

$^{19}$F-NMR (CDCl$_3$—CFCl$_3$): (For the major stereoisomer) δ —75.1(s, 3F) (For the minor isomer) δ —75.5(s, 3F)

IR (neat): 3465, 1716, 1260, 1200, 1180, 872 cm$^{-1}$

Mass [m/z (%)]: 277(M$^+$—OMe, 5), 128(11), 127(100), 125(15), 98(14), 97(16), 96(10), 95(49), 73(18), 69(15), 67(27), 59(24), 55(30), 43(20), 41(32), 39(15), 15(12)

Elemental analysis: Calculated for C$_{10}$H$_{13}$C$_{12}$F$_3$O$_3$: C, 38.86; H, 4.24% Found: C, 39.11; H, 4.30%

EXAMPLE 2

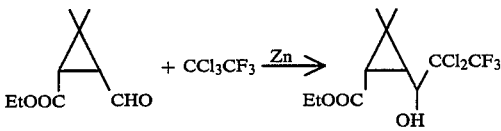

To a solution of 174 mg (1.02 mmol) of ethyl 2,2-dimethyl-3-formylcyclopropanecarboxylate in 1 ml of DMF, 96 mg (1.47 mmol) of zinc powder and 0.356 ml (3.00 mmol) of 1,1,1-trichlorotrifluoroethane were added, and the mixture was stirred at 0° C. for 2 hours and at 50° C. for 10 hours. Then, 2 ml of a saturated ammonium chloride aqueous solution was added thereto, and the mixture was extracted with diethyl ether (2 ml×3 times). The ethereal extract was dried over anhydrous magnesium sulfate, filtered and concentrated under reduced pressure to obtain a crude product. The crude product was purified by thin layer chromatography (silica gel, dichloromethane/hexane=1/1) to obtain 188 mg of ethyl 2,2-dimethyl-3-(1-hydroxy-2,2-dichloro-3,3,3trifluoropropyl)cyclopropanecarboxylate (a mixture of two stereoisomers in a ratio of 94:46).

Yield: 58% $^1$H-NMR (CDCl$_3$): (For the major stereoisomer) δ 1.22(s, 3H), 1.25(s, 3H), 1.29(t, 3H), 1.69(d, 1H), 1.94(dd, 1H), 2.63(broad, 1H), 3.82(broad d, 1H), 4.10-4.20(m, 2H) (For the minor isomer) δ 1.26(t, 3H), 1.30(s, 3H), 1.33(s, 3H), 1.70(d, 1H), 1.82(dd, 1H), 2.43(broad, 1H), 3.82(broad d, 1H), 4.10-4.20(m, 2H)

$^{19}$F-NMR (CDCl$_3$-CFCl$_3$): (For the major stereoisomer) δ—74.3(s, 3F) (For the minor isomer) δ—74.7(s, 3F)

IR (neat): 3465,1710, 1260, 1200 cm$^{-1}$

Mass[m/z (%)]: 277(M+$-EtO$, 11), 197(13), 142(11), 141(100), 125(16), 113(59), 98(20), 97(18), 95(30), 69(18), 67(22), 59(29), 55(41), 53(10), 43(30), 41(39), 39(17), 29(60), 27(18)

Elemental analysis: Calculated for C$_{11}$H$_{15}$Cl$_2$F$_3$O$_3$: C, 40.89; H, 4.68% Found: C, 41.02; H, 4.67%

EXAMPLE 3

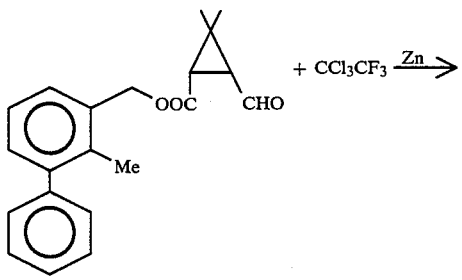

-continued

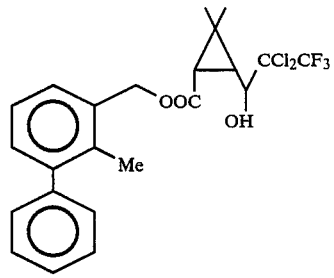

To a DMF (5 ml) solution of 1.61 g (5.00 mmol) of (2-methyl-3-phenylphenyl)methyl 2,2-dimethyl-3formylcyclopropanecarboxylate obtained in Reference Example 5, 0.890 ml (7.50 mmol) of trichlorotrifluoroethane and 391 mg (6.00 mmol) of zinc powder were added at 0° C. The mixture was stirred at 0° C. for 0.5 hour and at 45° C. for 3 hours, and then, 5 ml of a saturated ammonium chloride aqueous solution was added. After an addition of 20 ml of water, the mixture was extracted with diethyl ether (20 ml×3 times). The combined extract was dried over anhydrous magnesium sulfate, then filtered and concentrated under reduced pressure to obtain a crude product. The crude product was purified by column chromatography (silica gel, dichloromethane/hexane=1/1 to 1/0) to obtain 2.05 g of (2-methyl-3-phenylphenyl)methyl 2,2-dimethyl-3-(1-hydroxyl-2,2-dichloro-3,3,3-trifluoropropyl)cyclopropanecarboxylate (a mixture of two stereoisomers) as a colorless oily substance. Yield: 86%

A part of the product was purified by thin layer chromatography (silica gel, dichloromethane) to separate the two stereoisomers (A: colorless oil, R$_f$ 0.45 (CH$_2$Cl$_2$); B: colorless crystals, R$_f$ 0.33 (CH$_2$Cl$_2$)), respectively.

Physical properties of stereoisomer A $^1$H-NMR (CDCl$_3$) δ 1.26(s, 6H), 1.76(d, 1H), 1.97(dd, 1H), 2.19(s, 3H), 2.59(d, 1H), 3.81(dd, 1H), 5.18(s, 2H), 7.15-7.50(m, 8H)

$^{19}$F-NMR (CDCl$_3$-CFCl$_3$) δ —74.6(s, 3F)

IR (KBr): 3460(broad), 1728, 1711, 1257, 1220, 1200, 1180, 1113, 873, 760, 702 cm$^{-1}$ Mass [m/z (%)]: 476(M$^+$ +2, trace), 474(M$^+$, trace), 182(16), 181(100), 180(91), 179(10), 166(38), 165(40)

Elemental analysis: Calculated for C$_{23}$H$_{23}$Cl$_2$F$_3$O$_3$: C, 58.12; H, 4.88% Found: C, 57.99; H, 5.04%

Physical properties of stereoisomer B mp: 155°-156° C.

$^1$H-NMR (CDCl$_3$): δ 1.31(s, 3H), 1.32(s, 3H), 1.79(d, 1H), 1.93(dd, 1H), 2.19(s, 3H), 2.35(d, 1H), 3.82(t, 1H), 5.20 (s, 2H), 7.2-7.4(m, 8H)

$^{19}$F-NMR (CDCl$_3$-CFCl$_3$): δ —74.3(s, 3F)

IR (neat): 3425, 1711, 1260, 1227, 1200, 1184, 706 cm$^{-1}$

Mass [m/z (%)]: 277(trace), 198(14), 182(15), 181(100), 180(90), 179(17), 167(10), 166(40), 165(63), 152(10), 151(10), 57(22), 56(11), 43(17), 41(21), 28(20), 18(18)

Elemental analysis: Calculated for C$_{23}$H$_{23}$Cl$_2$F$_3$O$_3$: C, 58.12; H, 4.88% Found: C, 58.40; H, 4.96%

EXAMPLE 4

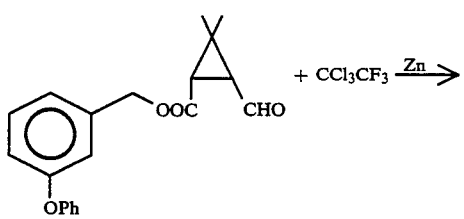

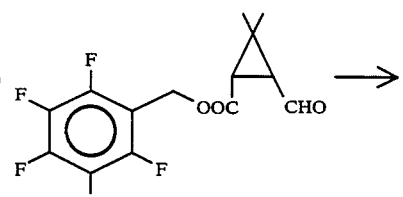

To a DMF (5 ml) solution of 1.62 g (5.00 mmol) of 3-phenoxyphenylmethyl 2,2-dimethyl-3-formylcyclopropanecarboxylate obtained in Reference Example 6, 0.890 ml (7.50 mmol) of 1,1,1-trichlorofluoroethane and 394 mg (6.03 mmol) of zinc powder were added at 0° C. The mixture was stirred at 0° C. for 0.5 hour and at 50° C. for 4 hours. The subsequent treatment was conducted in the same manner as in Example 3, whereby 1.77 g of 3-phenoxyphenylmethyl 2,2-dimethyl-3-(1-hydroxy-2,2-dichloro-3,3,3-trifluoropropyl)cyclopropanecarboxylate (a mixture of two stereoisomers) was obtained as a colorless oily substance.

Yield: 74%

A part of the product was subjected to thin layer chromatography (silica gel, dichloromethane) to separate the two stereoisomers ($R_f$ 0.70 and 0.55 ($CH_2Cl_2$)), respectively.

Physical properties of stereoisomer ($R_f$ 0.70 ($CH_2Cl_2$))

$^1$H-NMR ($CDCl_3$): δ 1.21(s, 3H), 1.24(s, 3H), 1.73(d, 1H), 1.94(dd, 1H), 2.44(d, 1H), 3.79(dd, 1H), 5.07(s, 2H), 6.8–7.4(m, 8H)

$^{19}$F-NMR ($CDCl_3$—$CFCl_3$): δ −75.0(s, 3F)

IR (neat): 3480, 1713, 1588, 1490, 1255, 1180, 870 cm$^{-1}$

Mass [m/z (%)]: 478(M$^+$+2. 3), 476(M$^+$, 4) 200(5), 184(16), 183(100), 77(6), 18(6)

Elemental analysis: Calculated for $C_{22}H_{21}Cl_2F_3O_4$C, 55.36; H, 4.43% Found: C, 55.39; H, 4.53%

Physical properties of stereoisomer ($R_f$ 0.55 ($CH_2Cl_2$))

$^1$H-NMR ($CDCl_3$): δ 1.28(s, 3H), 1.32(s, 3H), 1.74(d, 1H), 1.81(dd, 1H), 2.35(d, 1H), 3.78(dd, 1H), 5.06(s, 2H), 6.8–7.4(m, 8H)

$^{19}$F-NMR ($CDCl_3$—$CFCl_3$): δ −74.6(s, 3F)

IR (neat): 3470, 1728, 1713, 1587, 1491, 1254, 1200, 870 692 cm$^{-1}$

Mass[m/z (%)]: 478(M$^+$+2, 1.6), 476(M$^+$, 2.2), 184(16), 183(100), 89(6), 77(9), 55(10), 51(6), 41(6)

Elemental analysis: Calculated for $C_{22}H_{21}Cl_2F_3O_3$: C 55.36; H, 4.43% Found: C, 55.43; H, 4.52%

EXAMPLE 5

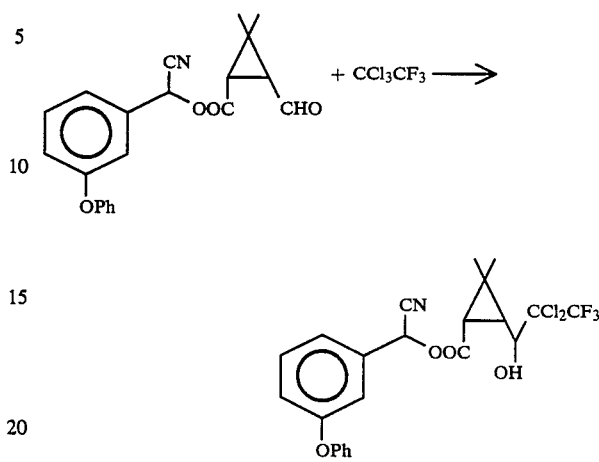

To a DMF (1 ml) solution of 360 mg (1.03 mmol) of cyano(3-phenoxyphenyl)methyl 2,2-dimethyl-3formyl-cyclopropanecarboxylate obtained in Reference Example 7, 0.18 ml (1.5 mmol) of 1,1,1-trichlorotrifluoroethane and 78 mg (1.2 mmol) of zinc powder were added at 0° C. The mixture was stirred at 50° C. for 22 hours. The subsequent treatment was conducted in the same manner as in Example 3, whereby 300 mg of cyano(3-phenoxyphenyl)methyl 2,2-dimethyl-3-(1-hydroxy-2,2-dichloro-3,3,3-trifluoropropyl)cyclopropanecarboxylate (a mixture of four stereoisomers) was obtained as a colorless oily substance.

Yield: 58%

$^1$H-NMR ($CDCl_3$): (For the mixture of the four stereoisomers) δ 1.19, 1.22, 1.24, 1.28, 1.31, 1.44(s, total 6H), 1.6–2.0(m, 2H), 2.6–3.2(broad 1H), 3.55–3.9(broad, 1H), 6.33, 6.38, 6.68, 6.70(s, total 1H), 6.7–7.6(m, 9H)

$^{19}$F-NMR ($CDCl_3$—$CFCl_3$) δ −74.0, −74.4, −74.6, −74.9(s, total 3F)

Mass [m/z (%)]: 503(M$^+$+2, 6), 501(M$^+$, 9), 279(25), 277(41), 209(35), 208(100), 197(82), 181(96), 180(20)

EXAMPLE 6

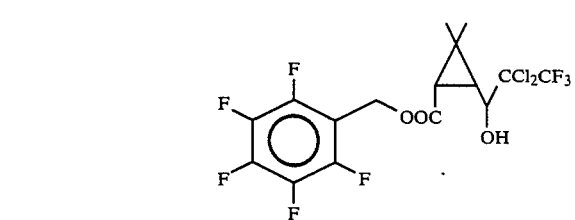

To a solution of 966 mg (3.00 mmol) of pentafluorophenylmethyl 2,2-dimethyl-3-formylcyclopropanecarboxylate obtained in Reference Example 8, in 3 ml of DMF, 0.54 ml (4.5 mmol) of 1,1,1-trichlorotrifluoroethane and 235 mg (3.60 mmol) of zinc powder, were added, and the mixture was stirred at 50° C. for 12 hours. The subsequent treatment was conducted in the same manner as in Example 3, whereby 1.02 g of pentafluorophenylmethyl 2,2-dimethyl-3-(1-hydroxy-2,2-dichloro-3,3,3-trifluoropropyl)cyclopropanecarboxylate (a mixture of two stereoisomers) was obtained as a colorless oily substance.

Yield: 71%

A part of the product was purified by thin layer chromatography (silica gel, dichloromethane) to isolate the two stereioisomers ($R_f$ values: 0.65, 0.53 ($CH_2Cl_2$)), respectively as colorless crystals.

Physical properties of stereoisomer ($R_f$ 0.65 ($CH_2Cl_2$))

mp: 75° C.

$^1$H-NMR (CDCl$_3$): δ 1.22(s, 3H), 1.24(s, 3H), 1.67(d, 1H), 1.95(dd, 1H), 2.43(d, 1H), 3.80(dd, 1H), 5.19(t, 2H)

$^{19}$F-NMR (CDCl$_3$—CFCl$_3$): δ −75.0(s, 3F)

IR (KBr): 1727, 1529, 1510, 1253, 1190, 1168, 1134, 1053, 940, 932 868 cm$^{-1}$

Mass [m/z (%)]: 476(M$^+$+2, trace), 474(M$^{30}$, trace), 293(35),

181(100), 59(11), 55(13)

Elemental analysis: Calculated for $C_{16}H_{12}Cl_2F_8O_3$: C, 40.44; H, 2.55% Found: C, 40.60; H, 2.61%

Physical properties of stereoisomer ($R_f$ 0.53 ($CH_2Cl_2$))

mp: 103°–4° C. $^1$H-NMR (CDCl$_3$): δ 1.31(s, 3H), 1.33(s, 3H), 1.69(d, 1H), 1.81(dd, 3H), 2.33(d, 1H), 3.77(dd, 1H), 5.17(t, 2H)

$^{19}$F-NMR (CDCl$_3$—CFCl$_3$): δ −74.6(s, 3F)

IR (KBr): 3440, 1721, 1526, 1509, 1260, 1223, 1200, 1188, 1178cm$^{-1}$

Mass [m/z (%)]: 293(29), 181(100), 55(13), 28(26)

Elemental analysis: Calculated for $C_{16}H_{12}Cl_2F_8O_3$: C, 40.44; H, 2.55% Found: C, 40.55; H, 2.64%

EXAMPLE 7

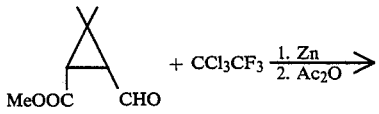

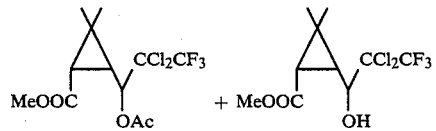

To a solution of 156 mg (1.00 mmol) of methyl 2,2-dimethyl-3-formylcyclopropanecarboxylate in 1 ml of DMF, 78 mg (1.19 mmol) of zinc powder and 0.177 ml (1.50 mmol) of 1,1,1-trichlorotrifluoroethane were added at 0° C., and the mixture was stirred at 0° C. for 30 minutes and at 50° C. for 10 hours. Then, 0.5 ml of acetic anhydride was added at room temperature, and the mixture was stirred for 10 minutes. After an addition of 2 ml of water, the mixture was extracted with diethyl ether (2 ml×5 times). The extract was dried over anhydrous magnesium sulfate, filtered and concentrated under reduced pressure to obtain a crude product. The crude product was purified by thin layer chromatography (silica gel, dichloromethane/hexane=⅔) to isolate 122 mg (35%) of methyl 2,2-dimethyl-3-(1-acetoxy-2,2-dichloro-3,3,3-trifluoropropyl)cyclopropanecarboxylate and 133 mg (43%) of methyl 2,2-dimethyl-3-(1-hydroxy-2,2-dichloro-3,3,3-trifluoropropyl)cyclopropanecarboxylate.

Physical properties of methyl 2,2-dimethyl-3-(1-acetoxy-2,2-dichloro-3,3,3-trifluoropropyl)cyclopropanecarboxylate $^1$H-NMR (CDCl$_3$): From the mixture of the two stereoisomers (For the major isomer) δ 1.24(s, 3H), 1.32(s, 3H), 1.60(d, 1H), 1.75(dd, 1H), 2.12(s, 3H), 3.69(s, 3H), 5.34(d, 1H) 7 15 (For the minor isomer) δ 1.17(s, 3H), 1.26(s, 3H), 2.14(s, 3H), 5.28(d, 1H) (Other peaks were not distinguishable from those of the major isomer)

$^{19}$F-NMR (CDCl$_3$—CFCl$_3$): δ −75.5(the major isomer, s, 3F) δ −74.7(minor isomer, s, 3F) IR (neat): 1768, 1736, 1374, 1262, 1233, 1206, 1032 cm$^{-1}$ Mass [m/z (%)]: 319(M$^+$−OMe, trace), 315(M$^+$−Cl, 3), 255(11), 127(54), 95(17), 73(10), 59(14), 43(100), 41(11), 18(18)

Elemental analysis: Calculated for $C_{12}H_{15}Cl_2F_3O_4$: C, 41.05; H, 4.31% Found: C, 40.97; H, 4.28%

EXAMPLE 8

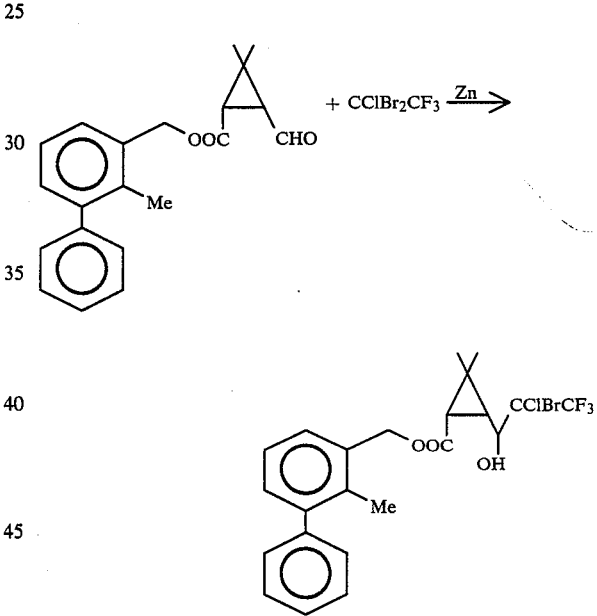

To a solution of 90 mg (0.28 mmol) of (2-methyl-3-phenylphenyl)methyl 2,2-dimethyl-3-formylcyclopropanecarboxylate obtained in Reference Example 5 and 148 mg (0.56 mmol) of 1-chloro-1,1-dibromotrifluoroethane in 0.5 ml of DMF, 38 mg (0.58 mmol) of zinc powder was added, and the mixture was stirred at room temperature for 40 minutes and at 50° C. for 18 hours. After an addition of 1 ml of a saturated ammonium chloride aqueous solution, the mixture was extracted with diethyl ether (2 ml×3 times). The extract was dried over anhydrous magnesium sulfate, then filtered and concentrated under reduced pressure. The product was purified by thin layer chromatography (silica gel, dichloromethane) to recover 25 mg (28%) of the starting material aldehyde and to obtain two stereoisomers of (2-methyl-3-phenylphenyl) methyl 2,2-dimethyl-3-(1-hydroxy-2-bromo-2-chloro-3,3,3-trifluoropropyl)cyclopropanecarboxylate in amounts of 2.6 mg (colorless oil, $R_f$ 0.46 ($CH_2Cl_2$)) and 25 mg (colorless crystals, $R_F$ 0.31 ($CH_2Cl_2$)), respectively (total yield: 35%, yield based on the consumed starting materials: 49%).

Physical properties of stereoisomer ($R_F$ 0.46 ($CH_2Cl_2$), colorless oil)

$^1$H-NMR (CDCl$_3$): δ 1.23(s, 3H), 1.78(d, 1H), 2.00(dd, 1H), 2.19(s, 3H), 2.60(broad, 1H), 5.18(s, 2H), 7.1–7.5(m, 8H) $^{19}$F-NMR (CDCl$_3$—CFCl$_3$): δ −73.0–70.9(s, total 3F) IR (neat): 3470, 1727, 1713, 1252, 1222, 1178, 763, 706 cm$^{-1}$ Mass [m/z (%)]: 520(M$^+$+2, trace), 518(M$^+$, trace), 182(15), 181(100), 180(90), 166(27), 165(29)

Physical properties of stereoisomer ($R_F$ 0.31 ($CH_2Cl_2$), colorless crystals)

$^1$H-NMR (CDCl$_3$—CFCl$_3$): δ 1.31(s, 3H), 1.33(s, 3H), 1.78(d, 1H), 1.89(dd, 1H), 2.18(s, 3H), 2.45(broad, 1H), 3.70(broad, 1H) 5.17(s, 2H), 7.1–7.5(m, 8H)

$^{19}$F-NMR (CDCl$_3$—CFCl$_3$): δ −72.7, −74.9(s, total 3F)

IR (KBr): 3420, 1712, 1252, 1226, 1199, 1176, 762, 704 cm$^{-1}$

Mass [m/z (%)]: 520(M$^+$+2, trace), 518(M$^+$, trace), 182(16), 181(100), 180(66), 179(12), 166(44), 165(53)

EXAMPLE 9

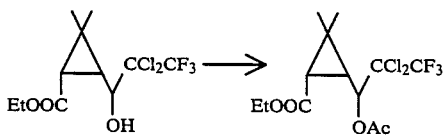

To 305 mg (0.944 mmol) of ethyl 2,2-dimethyl-3-(1-hydroxy-2,2-dichloro-3,3,3-trifluoropropyl)cyclopropanecarboxylate obtained in Example 2, 1 ml of pyridine and 1 ml of acetic anhydride, were added, and the mixture was stirred at room temperature for 5 hours. The reaction mixture was concentrated under reduced pressure, and then purified by column chromatography (silica gel, dichloromethane/hexane=1/1) to obtain 322 mg of ethyl 2,2-dimethyl-3-(1-acetoxy-2,2-dichloro-3,3,3trifluoropropyl)cyclopropanecarboxylate (a mixture of two stereoisomers (55:45)) as a colorless oily substance.

Yield: 93%

$^1$H-NMR (CDCl$_3$): (For the major isomer) δ 1.24(s, 3H), 1.26(t, 3H), 1.32(s, 3H), 1.59(d, 1H), 2.06(dd, 1H), 2.13(s, 3H), 4.09–4.22(m, 2H), 5.35(d, 1H) (For the minor isomer) δ 1.17(s, 3H), 1.26(s, 3H), 1.26(t, 3H), 1.77(d, 1H), 2.01(dd, 1H), 2.15(s, 3H), 4.09–4.22(m, 2H), 5.28(d, 1H)

$^{19}$F-NMR (CDCl$_3$—CFCl$_3$): (For the major isomer) δ −75.5(s, 3F) (For the minor isomer) δ −74.6(s, 3F)

IR (neat): 5 1769, 1732, 1374, 1262, 1250, 1208, 1188, 1030 cm$^{-1}$

Mass [m/z (%)]: 331((M+2)−Cl, trace), 329(M$^+$−Cl, 2.7), 197(11), 141(37), 113(18), 43(100), 29(26), 28(23), 18(15) 18(18)

Elemental analysis: Calculated for C$_{13}$H$_{17}$Cl$_2$F$_3$O$_4$: C, 42.76; H, 4.69% Found: C, 42.75; H, 4.59%

EXAMPLE 10

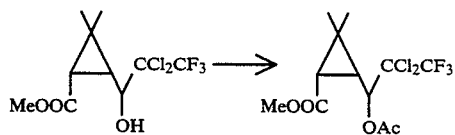

To 50 mg (0.16 mmol) of methyl 2,2-dimethyl-3-(1-hydroxy-2,2-dichloro-3,3,3-trifluoropropyl)cyclopropanecarboxylate obtained in Example 1, 0.2 ml of acetic anhydride and 0.2 ml of pyridine were added, and the mixture was left overnight at room temperature. In the same manner as in Example 9, 53 mg of methyl 2,2-dimethyl-3-(1-acetoxy-2,2-dichloro-3,3,3-trifluoropropyl)cyclopropanecarboxylate was obtained as a colorless oily substance. Yield: 93%. The physical property values were the same as those in Example 7.

EXAMPLE 11

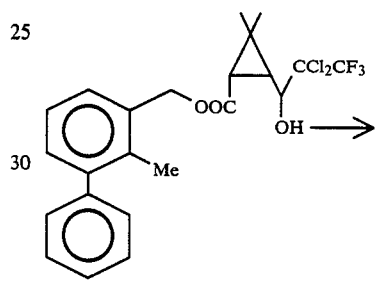

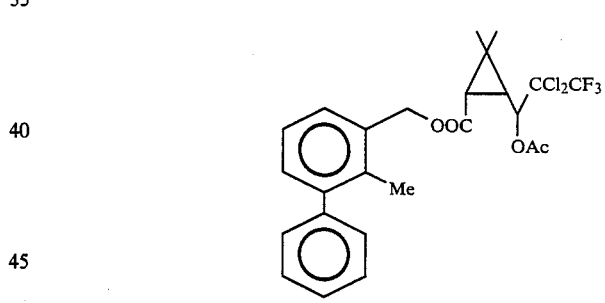

To 118 mg (0.248 mmol) of stereoisomer A (colorless oil, $R_F$ 0.45 ($CH_2Cl_2$)) of (2-methyl-3-phenylphenyl)-methyl 2,2-dimethyl-3-(1-hydroxy-2,2-dichloro-3,3,3-trifluoropropyl)cyclopropanecarboxylate obtained in Example 3, 0.3 ml of pyridine and 0.3 ml of acetic anhydride were added, and the mixture was left at room temperature for 4 hours. The reaction mixture was concentrated under reduced pressure and purified by thin layer chromatography (silica gel, dichloromethane/hexane=⅔) to obtain 125 mg of (2-methyl-3-phenylphenyl)methyl 2,2-dimethyl-3-(1-hydroxy-2,2-dichloro-3,3,3-trifluoropropyl)cyclopropanecarboxylate.

Yield: 98%

$R_F$ 0.46 ($CH_2Cl_2$/hexane=1/1)

$^1$H-NMR (CDCl$_3$): δ 1.27(s, 3H), 1.33(t, 3H), 1.70(d, 1H), 2.09(s, 3H), 2.13(dd, 1H), 2.22(s, 3H), 5.25(s, 2H), 5.40(d, 1H), 7.2–7.5(m, 8H)

$^{19}$F-NMR (CDCl$_3$—CFCl$_3$): δ −75.5(s, 3F)

IR (neat): 1754, 1749, 1730, 1256, 1228, 1204, 1188, 1160 1028, 758, 702

Mass [m/z (%)]: 518(M++2, trace), 516(M+, trace), 182(15), 181(100), 180(86), 166(28), 165(30), 43(38)

Elemental analysis: Calculated for $C_{25}H_{25}Cl_2F_3O_4$: C, 58.04; H, 4.87% Found: C, 58.31; H, 4.91%

To 66 mg (0.14 mmol) of the other stereoisomer (R$_f$0.33 (CH$_2$Cl$_2$)) of the starting material, 0.2 ml of pyridine and 0.2 ml of acetic anhydride, were added, and the mixture was left at room temperature for 3 hours. The work up was conducted in the same manner, whereby 72 mg of the acetylated product was obtained.

Yield: 100%

Rf: 0.39 (CH$_2$Cl$_2$/hexane=1/1) $^1$H-NMR (CDCl$_3$): δ 1.18(s, 3H), 1.30(s, 3H), 1.85(d, 1H), 2.05(dd, 1H), 2.14(s, 3H), 2.20(s, 3H), 5.19(s, 2H), 5.24(s, 1H), 7.1-7.5(m, 8H)

$^{19}$F-NMR (CDCl$_3$—CFCl$_3$): δ −74.8(s, 3F)

IR (neat):
1770, 1730, 1260, 1230-1160(broad) 1031, 842, 762, 704 cm$^{-1}$

Mass [m/z (%)]: 518(M++2, trace), 516(M+trace), 182(15), 181(100), 180(74), 166(24), 165(25), 43(31)

Elemental analysis: Calculated for $C_{25}H_{25}Cl_2F_3O_4$: C, 58.04; H, 4.87% Found: C, 58.13; H, 4.90%

EXAMPLE 12

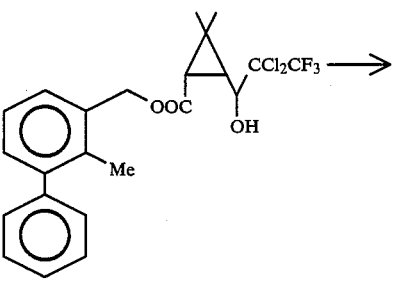

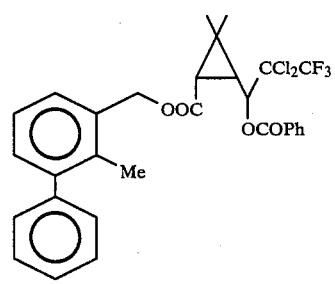

To a solution of 390 mg (0.821 mmol) of (2-methyl-3-phenylphenyl)methyl 2,2-dimethyl-3-(1-hydroxy-2,2-dichloro-3,3,3-trifluoropropyl)cyclopropanecarboxylate obtained in Example 3, in 2 ml of diethyl ether, 0.114 ml (0.98 mmol) of benzoyl chloride and 0.137 ml of triethylamine, were added, and the mixture was stirred at room temperature for 12 hours. Then, 0.23 ml of benzoyl chloride and 0.28 ml of triethylamine were further added, and the mixture was stirred overnight at room temperature. After an addition of 5 ml of hexane, the inorganic salts are filtered off, and the filtrate was concentrated under reduced pressure. The product was purified by thin layer chromatography (silica gel, dichloromethane/hexane=1/1) to obtain 175 mg of (2-methyl-3-phenylphenyl)methyl 2,2-dimethyl-3-(1-benzoyloxy-2,2-dichloro-3,3,3-trifluoropropyl)cyclopropanecarboxylate as a colorless oily substance.

Yield: 37%

$^1$H-NMR (CDCl$_3$): δ 1.32(s, 3H), 1.40(s, 3H), 1.81(d, 1H), 2.21(dd, 1H), 5.07(s, 2H), 5.58(d, 1H), 7.0-7.6(m, 11H), 7.9-8.1(2H)

$^{19}$F-NMR (CDCl$_3$—CFCl$_3$) δ −75.5(s, 3F)

IR (neat): 1732, 1450, 1068, 1028, 889, 836, 830, 799, 762, 706 cm$^{-1}$

Mass [m/z (%)]: 580(M++2, trace), 578(M+ trace), 182(16), 181(100), 180(94), 179(10), 166(35), 165(36), 105(35), 77(10)

Elemental analysis: Calculated for $C_{30}H_{27}Cl_2F_3O_4$: C, 62.19; H, 4.70% Found: C, 62.26; H, 4.78%

EXAMPLE 13

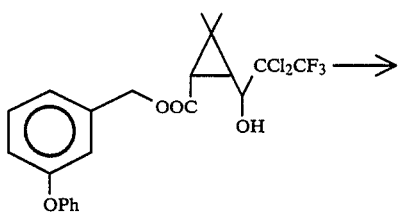

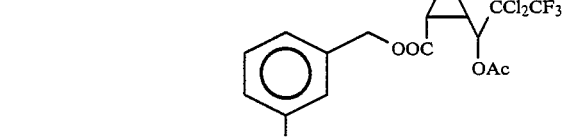

To a solution of 954 mg (2.00 mmol) of (3-phenoxyphenyl)methyl 2,2-dimethyl-3-(1-hydroxy-2,2-dichloro-3,3,3-trifluoropropyl)cyclopropanecarboxylate obtained in Example 4, in 2 ml of pyridine, 2 ml of acetic anhydride was added, and the mixture was stirred at room temperature for 5 hours. The reaction mixture was concentrated under reduced pressure, and purified by column chromatography (silica gel, dichloromethane/hexane =1/1) to obtain 1.02 g of (3-phenoxyphenyl)methyl 2,2-dimethyl-3-(1-acetoxy-2,2-dichloro-3,3,3-trifluoropropyl)cyclopropanecarboxylate as a colorless oily substance.

Yield: 98%

$^1$H-NMR (CDCl$_3$): From the spectrum of the mixture of two stereoisomers (For the major stereoisomer) δ 1.22(s, 3H), 1.31(s, 3H), 1.66(d, 1H), 2.07(s, 3H), 2.08(dd, 1H), 5.11(s, 2H), 5.35(d, 1H), 6.90-7.15(m, 5H), 7.25-7.40(m, 4H) (For the minor isomer) δ 1.16(s, 3H), 1.24 (s, 3H), 1.84(d, 1H), 2.03(dd, 1H), 2.13(s, 3H), 5.09(d, 1H), 5.12(d, 1H), 5.28(d, 1H), 6.90-7.15(m, 5H), 7.25-7.40(m, 4H)

$^{19}$F-NMR (CDCl$_3$—CFCl$_3$): (For the major stereoisomer) δ −76.0(s, 3F) (For the minor isomer) δ −75.2(s, 3F)

IR (neat): 1767, 1732, 1588, 1492, 1446, 1374, 1255, 1205, 1168, 1028, 692 cm$^{-1}$ Mass [m/z (%)]: 521(M++3, 1), 520(M++2, 3), 519(M++1, 1), 518(M+, 4), 184(16), 183(100), 43(55)

Elemental analysis: Calculated for $C_{24}H_{23}Cl_2F_3O_5$: C, 55.51; H, 4.46% Found: C, 55.52; H, 4.67%

EXAMPLE 14

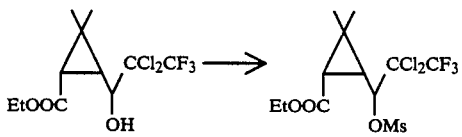

To a solution of 135 mg (0.794 mmol) of ethyl 2,2-dimethyl-3-(1-hydroxy-2,2-dichloro-3,3,3-trifluoropropyl)cyclopropanecarboxylate obtained in Example 2, in 2 ml of diethyl ether, 0.073 ml (0.94 mmol) of methanesulfonyl chloride and 0.133 ml (0.95 mmol) of triethylamine, were added, and the mixture was stirred at room temperature for 2 hours. After an addition of 5 ml of hexane to the mixture, the precipitated inorganic salt was filtered off, and the filtrate was concentrated under reduced pressure. The product was purified by thin layer chromatography (silica gel, dichloromethane/hexane=1/1) to obtain 157 mg of ethyl 2,2-dimethyl-3-(1-methanesulfonyloxy-2,2-dichloro-3,3,3trifluoropropyl)cyclopropanecarboxylate as a colorless oily substance.

Yield: 80%

$^1$H-NMR (CDCl$_3$): For the spectrum of the mixture of two stereoisomers: δ 1.2–1.4(9H), 1.8–2.2(2H), 3.12, 3.16(s, total 3H), 4.14(q, 2H), 4.89, 4.90(d, total 1H)

$^{19}$F-NMR (CDCl$_3$ —CFCl$_3$): δ −74.8, −73.8(s, total 3F)

IR (neat): 1730, 1368, 1257, 1232, 1180, 932, 896, 809 cm$^{-1}$

Mass [m/z (%)]: 521(M$^+$+2)−OEt, 5), 355(M+OEt, 7), 269(12), 233(18), 232(10), 231(24), 199(33), 198(11), 197(100), 195(19), 175(11), 161(32), 159(20), 141(69), 137(15), 113(28), 97(12), 95(14), 80(10), 79(26), 69(10), 67(13), 59(17), 43(14), 41(28), 39(11), 29(70), 27(15), 15(14)

Elemental analysis: Calculated for C$_{12}$H$_{17}$Cl$_2$F$_3$O$_5$S: C, 35.92; H, 4.27% Found: C, 35.86; H, 4.27%

EXAMPLE 15

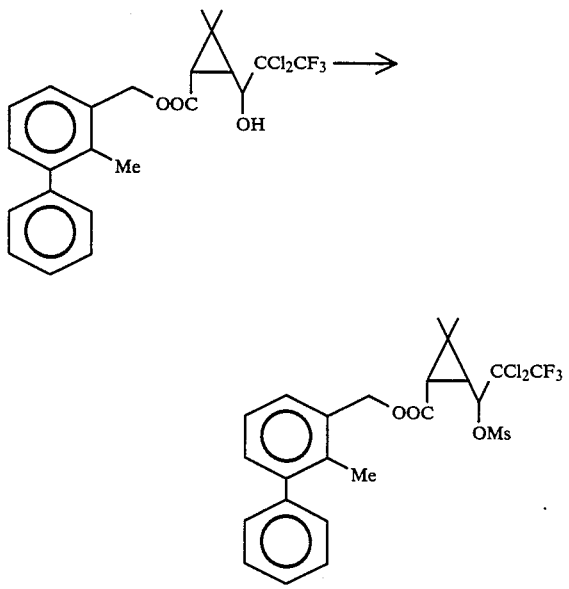

To a solution of 406 mg (0.855 mmol) of (2-methyl-3phenylphenyl)methyl 2,2-dimethyl-3-(1-hydroxy-2,2-dichloro-3,3,3-trifluoropropyl)cyclopropanecarboxylate obtained in Example 3, in 2 ml of diethyl ether, 0.079 ml (1.0 mmol) of methanesulfonyl chloride and 0.143 ml (1.0 mmol) of triethylamine, were added, and the mixture was stirred at room temperature for 1 hour. After an addition of 5 ml of hexane to the mixture, the precipitated inorganic salt was filtered off, and the filtrate was concentrated under reduced pressure. The product was purified by thin layer chromatography (silica gel, dichloromethane/hexane=1/1) to obtain 458 mg of (2-methyl-3-phenylphenyl)methyl 2,2-dimethyl-3-(1-methanesulfonyloxy-2,2-dichloro-3,3,3-trifluoropropyl)cyclopropanecarboxylate as a colorless oily substance.

Yield: 97%

$^1$H-NMR (CDCl$_3$): For the spectrum of the mixture of two stereoisomers: δ 1.26, 1.31, 131, 1.38(s, total 6H), 1.9–2.3(2H), 2.18, 2.20(s, total 3H), 3.03, 3.13(s, total 3H), 4.88, 4.99(d, 1H), 5.19(s, 2H), 7.1–7.5(m, 8H)

$^{19}$F-NMR (CDCl$_3$—CFCl$_3$): δ −73.7, −74.8(s, total 3F)

IR (neat): 1729, 1360, 1252, 1230–1160(broad), 928, 808, 761, 704 cm$^{-1}$

Mass [m/z (%)]: 554(M$^+$+2, trace), 552(M$^+$, trace), 182(17), 181(100), 180(45), 179(11), 166(32), 165(33)

Elemental analysis: Calculated for C$_{24}$H$_{25}$Cl$_2$F$_3$O$_5$S: C, 52.09; H, 4.55% Found: C, 52.02; H, 4.68%

EXAMPLE 16

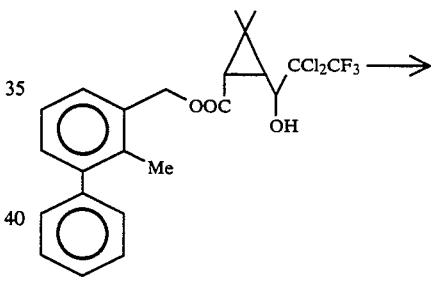

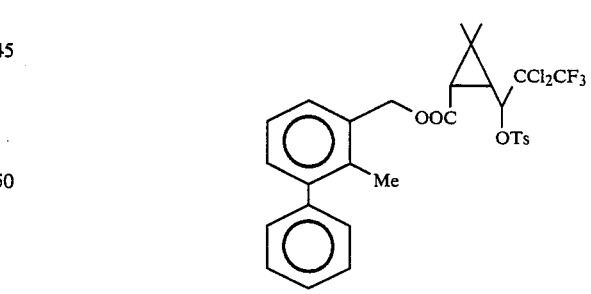

To a solution of 97 mg (0.20 mmol) of (2-methyl-3-phenylphenyl)methyl 2,2-dimethyl-3-(1-hydroxy-2,2-dichloro-3,3,3-trifluoropropyl)cyclopropanecarboxylate obtained in Example 3 and dissolved in 0.5 ml of diethyl ether and 0.5 ml of DMF, 12 mg (0.25 mmol) of sodium hydride and 39 mg (0.20 mmol) of p-toluenesulfonyl chloride were added, and the mixture was stirred overnight at room temperature. After an addition of 1 ml of a saturated ammonium chloride aqueous solution, the mixture was extracted with diethyl ether (2 ml×3 times). The extract was dried over anhydrous magnesium sulfate, then filtered and concentrated under reduced pressure to obtain a crude produce. The crude product was purified by thin layer chromatography (silica gel, dichloromethane/hexane=⅓) to obtain 83 mg of (2-methyl-3-phenylphenyl)methyl 2,2-dimethyl-3-(1-tosyloxy-2,2-dichloro-3,3,3-trifluoropropyl)cyclopropanecarboxylate as a colorless oily substance.

Yield: 65%

$^1$H-NMR (CDCl$_3$): For the spectrum of the mixture of two stereoisomers: δ 1.23, 1.23, 1.33, 1.37(s, total 6H), 1.9–2.3(2H), 2.19, 2.21(s, total 3H), 2.37, 2.43(s, total 3H), 4.85–5.05(1H), 5.15, 5.16(s, total 2H), 7.1–7.4(m, 10H), 7.6–7.9(m, 2H)

$^{19}$F-NMR (CDCl$_3$—CFCl$_3$): δ −74.6, −73.3(total 3F)

IR (neat): 1730, 1600, 1460, 1387, 1114, 1096 560 cm$^{-1}$

Mass [m/z (%)]: 630(M$^+$+1, trace), 628(M$^+$, trace), 182(15), 181(100), 180(74), 166(30), 165(28)

Elemental analysis: Calculated for C$_{30}$H$_{29}$Cl$_2$F$_3$O$_5$S: C, 57.24; H, 4.64% Found: C, 57.23; H, 4.70%

EXAMPLE 17

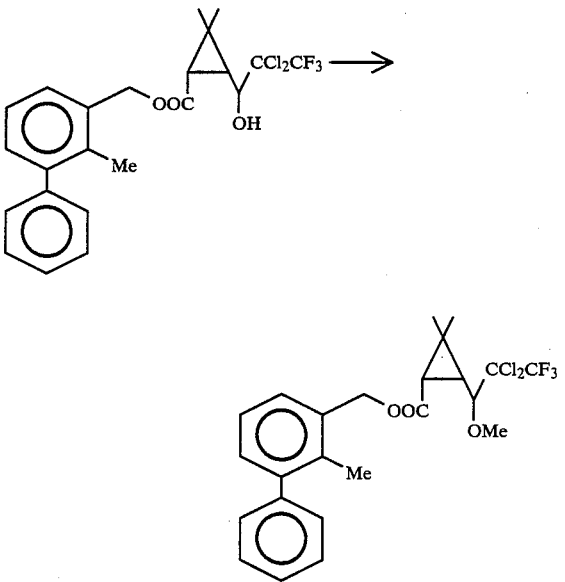

To a solution of 104 mg (0.219 mmol) of (2-methyl-3-phenylphenyl)methyl 2,2-dimethyl-3-(1-hydroxy-2,2-dichloro-3,3,3-trifluoropropyl)cyclopropanecarboxylate obtained in Example 3 and dissolved in 0.5 ml of DMF, 0.5 ml of methyl iodide and 12 mg (0.25 mmol) of sodium hydride were added, and the mixture was stirred at room temperature for 30 minutes. After an addition of 1 ml of a saturated ammonium chloride aqueous solution, the mixture was extracted with diethyl ether (2 ml×4 times). The extract was dried over anhydrous magnesium sulfate, then filtered and concentrated under reduced pressure. The product was purified by thin layer chromatography to obtain 106 mg of (2-methyl-3-phenylphenyl)methyl 2,2-dimethyl-3-((1-1-methoxy-2,2-dichloro-3,3,3,-trifluoropropyl)cyclopropanecarboxylate as a colorless oil.

Yield: 99%

$^1$H-NMR (CDCl$_3$): For the spectrum of the mixture of two stereoisomers: δ 1.25, 1.28, 1.31, 1.33(s, total 3H), 1.75–1.90(1H), 1.90–2.20(1H), 2.19, 2.21(s, total 3H), 3.4–3.7(1H), 3.50, 3.52(s, total 3H), 5.19(s, 2H), 7.1–7.5(m, 8H)

$^{19}$F-NMR (CDCl$_3$—CFCl$_3$):δ −75.0, −74.6(s, total 3F)

IR (neat): 1730, 1256, 1205, 1182, 1164, 761, 703 cm$^{-1}$

Mass [m/z (%)]: 490(M$^+$+2, trace), 488(M$^+$, trace), 182(16), 181(100), 180(74), 166(23), 165(24)

Elemental analysis: Calculated for C$_{24}$H$_{25}$Cl$_2$F$_3$O$_3$: C, 58.91; H, 5.15% Found: C, 58.82; H, 5.19%

REFERENCE EXAMPLE 9

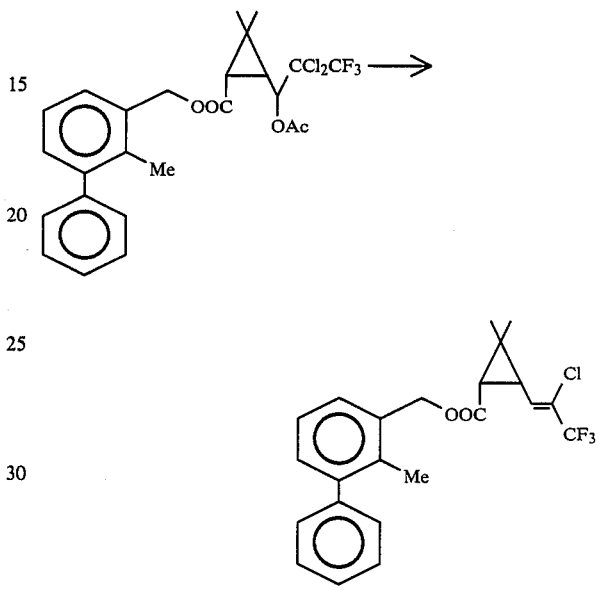

To a solution of 38.4 mg (0.074 mmol) of the stereoisomer [R$_F$0.39 (CH$_2$Cl$_2$/hexane=1/1)] of (2-methyl-3-phenylphenyl)methyl 2,2-dimethyl-3-(1-acetoxy-2,2-dichloro-3,3,3-trifluoro-propyl)cyclopropanecarboxylate obtained in Example 11 and dissolved in 0.3 ml of DMF, 6 mg of zinc powder was added, and the mixture was stirred at 60° C. for 2.5 hours. After an addition of 2 ml of diethyl ether and 2 ml of pentane to the mixture, the inorganic salt was filtered off through a silica gel short column. The silica gel was washed with diethyl ether, and the organic layers were combined and concentrated under reduced pressure. The product was purified by thin layer chromatography (silica gel, dichloromethane/hexane=⅓) to obtain 29.8 mg of (2-methyl-3-phenylphenyl)methyl 2,2-dimethyl-3-(2-chloro-3,3,3-trifluoro-1-propenyl)cyclopropanecarboxylate as a colorless oily substance.

Yield: 95%. Based on a $^1$H-NMR spectrum, (Z):(E) was found to be 89:11.

$^1$H-NMR (CDCl$_3$): (From the mixture of (Z) and (E)) For (Z) isomer: δ 1.23(s, 3H), 1.35(s, 3H), 1.82 (d, 1H), 2.22(s, 3H), 2.42(dd, 1H), 5.20(s, 2H), 6.10(dq, 1H), 7.15–7.5(m, 8H) For (E) isomer: δ 1.23(s, 3H), 1.29(s, 3H), 5.85(d, 1H) (Other signals were not distinguishable from those of (Z) isomer)

$^{19}$F-NMR (CDCl$_3$—CFCl$_3$): (Z) isomer, δ −68.7(s, 3F) (E) isomer, δ −62.5(s, 3F)

IR (neat): 1732, 1284, 1228, 1167, 1144, 1116, 765, 706 cm$^{-1}$

Likewise, the same reduction products were obtained also from the less polar stereoisomer [R$_F$ 0.46 (CH$_2$Cl$_2$/hexane=1/1)] of the acetate. (Z):(E)=93:7 (from the $^1$H-NMR data)

REFERENCE EXAMPLE 10

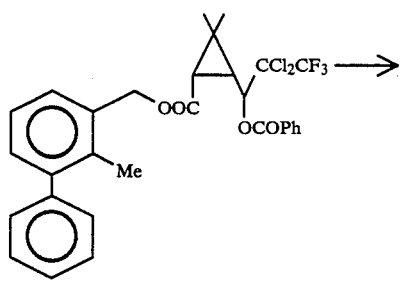

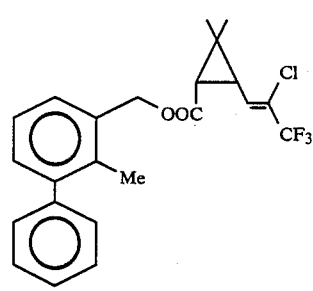

To a solution of 56 mg (0.097 mmol) of (2-methyl-3-phenylphenyl)methyl 2,2-dimethyl-3-(1-benzoyloxy-2,2-dichloro-3,3,3-trifluoropropyl)cyclopropanecarboxylate obtained in Example 12 and dissolved in 0.1 ml of DMF, 8 mg (0.12 mmol) of zinc powder was added, and the mixture was stirred at 60° C. for 6 hours. The subsequent operation was carried out in the same manner as in Reference Example 9, whereby 40 mg of (2-methyl-3-phenylphenyl)methyl 2,2-dimethyl-3-(2-chloro-3,3,3-trifluoro-1-propenyl)cyclopropanecarboxylate was obtained. Yield: 98%. (Z):(E)=86:14.

REFERENCE EXAMPLE 11

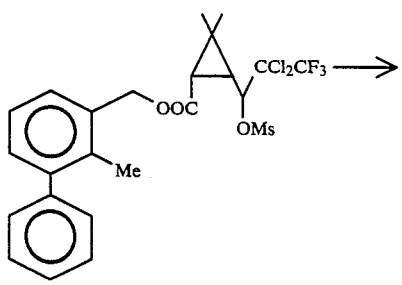

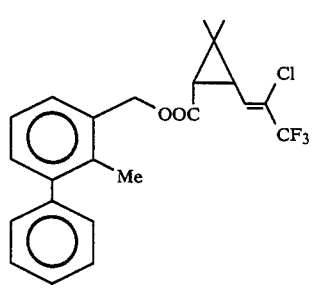

To a solution of 170 mg (0.0307 mmol) of (2-methyl-3-phenylphenyl)methyl 2,2-dimethyl-3-(1-methyloxy-2,2-dichloro-3,3,3-trifluoropropyl)cyclopropane carboxylate obtained in Example 15 and dissolved in 0.5 ml of DMF, 21 mg (0.32 mmol) of zinc powder was added, and the mixture was stirred at 50° C. for 1 hour. The subsequent operation was conducted in the same manner as in Reference Example 9, whereby 123 mg of (2-methyl-3-phenylphenyl)methyl 2,2-dimethyl-3-(2-chloro-3,3,3-trifluoro-1-propenyl)cyclopropanecarboxylate was obtained.
Yield: 95%. (Z):(E)=88:12.

REFERENCE EXAMPLE 12

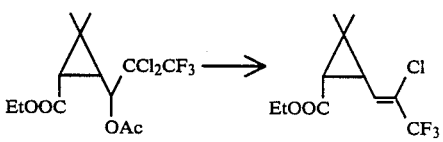

To a solution of 183 mg (0.500 mmol) of ethyl 2,2-dimethyl-3-(1-acetoxy-2,2-dichloro-3,3,3-trifluoropropyl)cyclopropanecarboxylate obtained in Example 9, in 0.5 ml of DMF, 35 mg (0.54 mmol) of zinc powder was added, and the mixture was stirred at 50° C. for 4 hours. After an addition of 1 ml of a saturated ammonium chloride aqueous solution, the mixture was extracted with diethyl ether (1 ml×5 times). The extract was dried over anhydrous magnesium sulfate, then filtered and concentrated under reduced pressure. The product was purified by thin layer chromatography (silica gel, dichloromethane/hexane=¼) to obtain 116 mg of ethyl 2,2-dimethyl-3-(2-chloro-3,3,3-trifluoro-1-propenyl)-cyclopropane carboxylate as a colorless oil.
Yield: 86%. (Z):(E)=6:1.

$^1$H-NMR (CDCl$_3$): From the spectrum of (Z):(E)=6:1 For (Z) isomer: δ 1.24(s, 3H), 1.28(t, 3H), 1.33(s, 3H), 1.77(d, 1H), 2.40(ddq, 1H), 4.10–4.22 (m, 2H), 6.15(dq, 1H) For (E) isomer: δ 1.21(s, 3H), 1.27(t, 3H), 1.28(s, 3H), 4.10–4.22(m, 2H), 5.89(d, 1H)

$^{19}$F-NMR (CDCl$_3$—CFCl$_3$) For (Z) isomer: δ −68.9(s, 3F) For (E) isomer: δ −62.5(d, 1F)

IR (neat): 1731, 1286, 1229, 1176, 1142 cm$^{-1}$

REFERENCE EXAMPLE 13

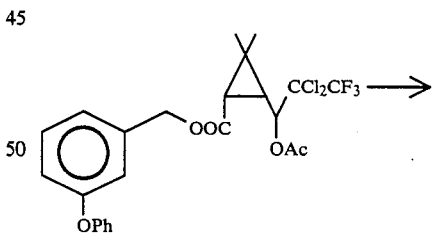

To a solution of 260 mg (0.501 mmol) of (3-phenoxyphenyl)methyl 2,2-dimethyl-3-(1-acetoxy-2,2-dichloro-3,3,3-trifluoropropyl)cyclopropanecarboxylate obtained in Example 13, in 1 ml of DMF, 35 mg (0.521 mmol) of zinc powder was added, and the mixture was stirred at 60° C. for 6 hours. The subsequent operation was conducted in the same manner as in Reference Example 9, whereby 157 mg of (3-phenoxyphenyl)methyl 2,2-dimethyl-3-(2-chloro-3,3,3-trifluoro-1-propenyl)cyclopropanecarboxylate was obtained.

Yield: 74%.

$^1$H-NMR (CDCl$_3$): From the spectrum of (Z):(E)=6:1 For (Z) isomer: δ 1.21(s, 3H), 1.30(s, 3H), 1.76(d, 1H), 2.37(dd, 1H), 5.06(s, 2H), 6.08(d, 1H), 6.8-7.4(m, 8H) For (E) isomer: δ1.22(s, 3H), 1.70(d, 1H), 5.82(d, 1H)

$^{19}$F-NMR (CDCl$_3$—CFCl$_3$): For (Z) isomer: δ −69.2(s, 3F) For (E) isomer: δ −62.9(s, 3F)

IR (neat): 1732, 1588, 1492, 1283, 1256, 1221, 1167, 1140, 1113, 693 cm$^{-1}$

We claim:

1. A 2,2-dimethylcyclopropanecarboxylic acid derivative having the formula:

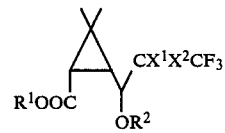

wherein $R^1$ is selected from the group consisting of methyl, ethyl, t-butyl, phenyl, benzyl, 2-methyl-3phenylbenzyl, 3-phenoxybenzyl, cyano(3-phenoxyphenyl)methyl and pentafluorophenylmethyl; $R^2$ is selected from the group consisting of acetyl, benzoyl and methyl; and each of $X^1$ and $X^2$ is chlorine or bromine.

2. The derivative according to claim 1, wherein $R^1$ is methyl, ethyl, (2-methyl-3-phenylphenyl)methyl, (3-phenoxyphenyl)methyl, cyano(3-phenoxyphenyl)methyl or pentafluorophenylmethyl, $R^2$ is acetyl or methyl, and each of $X^1$ and $X^2$ is chlorine.

* * * * *